(12) United States Patent
Heinonen

(10) Patent No.: US 9,572,952 B2
(45) Date of Patent: Feb. 21, 2017

(54) HOUSING FOR SOLID, FLUIDAL SUBSTANCE FOR REMOVING AN UNDESIRED RESPIRATORY GAS COMPONENT OF A RESPIRATORY GAS FLOW AND AN ARRANGEMENT FOR VENTILATING LUNGS OF A SUBJECT

(75) Inventor: Erkki Heinonen, Helsinki (FI)

(73) Assignee: Vyaire Medical Comsumables LLC, Yorba Linda, CA (US)

( * ) Notice: Subject to any disclaimer, the term of this patent is extended or adjusted under 35 U.S.C. 154(b) by 0 days.

(21) Appl. No.: 13/403,354

(22) Filed: Feb. 23, 2012

(65) Prior Publication Data

US 2013/0074837 A1 Mar. 28, 2013

(30) Foreign Application Priority Data

Feb. 25, 2011 (EP) .................................... 11155922

(51) Int. Cl.
*A62B 19/00* (2006.01)
*A61M 16/22* (2006.01)
(Continued)

(52) U.S. Cl.
CPC ......... *A61M 16/22* (2013.01); *A61M 16/0057* (2013.01); *A61M 16/104* (2013.01);
(Continued)

(58) Field of Classification Search
CPC .... A61M 16/22; A61M 16/18; A61M 16/208; A61M 16/0057; A61M 16/104; A61M 16/105; A61M 16/12; A62B 19/00; A62B 19/02
(Continued)

(56) References Cited

U.S. PATENT DOCUMENTS 1,843,446 A * 2/1932 Drager ................... A62B 19/00
                                                                128/206.17
3,403,981 A * 10/1968 Lemcke et al. ............... 422/120
(Continued)

FOREIGN PATENT DOCUMENTS

| DE | 702099 C | 1/1941 |
| GB | 2420507 A | 5/2006 |
| WO | 96/15027 A1 | 5/1996 |

OTHER PUBLICATIONS

Chinese First Office Action for Chinese Application No. 201210052766.5, dated Apr. 3, 2015, 12 pages.
(Continued)

*Primary Examiner* — Justine Yu
*Assistant Examiner* — Timothy Stanis
(74) *Attorney, Agent, or Firm* — McDermott Will & Emery LLP

(57) ABSTRACT

A housing for a solid, fluidal substance for removing an undesired respiratory gas component of a respiratory gas flow, the housing comprising a space for receiving the solid, fluidal substance, a wall surrounding part of the space, a first separator surrounding part of the space, the first separator being configured to allow the respiratory gas to flow and to prevent the solid, fluidal substance from escaping from the space through the first separator, a second separator surrounding part of the space, the second separator being configured to allow the respiratory gas to flow and to prevent the solid, fluidal substance from escaping from the space through the second separator; and a limiter disposed between the first separator and the second separator, the limiter being configured to limit movement of the solid, fluidal substance inside the space.

8 Claims, 5 Drawing Sheets

(51) Int. Cl.
| | |
|---|---|
| *B01D 53/04* | (2006.01) |
| *B01D 53/62* | (2006.01) |
| *B01D 53/82* | (2006.01) |
| *A61M 16/00* | (2006.01) |
| *A61M 16/10* | (2006.01) |
| *A61M 16/12* | (2006.01) |
| *A61M 16/18* | (2006.01) |
| *A61M 16/20* | (2006.01) |

(52) U.S. Cl.
CPC .......... *A61M 16/105* (2013.01); *A61M 16/12* (2013.01); *A62B 19/00* (2013.01); *B01D 53/0407* (2013.01); *B01D 53/62* (2013.01); *B01D 53/82* (2013.01); *A61M 16/18* (2013.01); *A61M 16/208* (2013.01); *B01D 53/0415* (2013.01); *B01D 2251/304* (2013.01); *B01D 2251/306* (2013.01); *B01D 2251/604* (2013.01); *B01D 2257/504* (2013.01); *B01D 2259/4533* (2013.01); *Y02C 10/04* (2013.01); *Y02C 10/08* (2013.01)

(58) Field of Classification Search
USPC .... 128/202.26, 205.12, 205.27, 205.28, 2.26
See application file for complete search history.

(56) References Cited

U.S. PATENT DOCUMENTS

| | | | | |
|---|---|---|---|---|
| 3,566,867 | A | * | 3/1971 | Dryden .................. 128/205.28 |
| 3,721,238 | A | * | 3/1973 | Wise et al. .............. 128/205.28 |
| 3,752,654 | A | | 8/1973 | Johannisson et al. |
| 3,942,524 | A | * | 3/1976 | Li et al. .................. 128/202.26 |
| 4,717,549 | A | * | 1/1988 | Malafosse et al. .......... 422/122 |
| 5,765,550 | A | | 6/1998 | Psaros et al. |
| 6,619,289 | B1 | * | 9/2003 | Mashak .................. 128/205.28 |
| 7,424,889 | B2 | | 9/2008 | Mashak |
| 7,487,776 | B2 | | 2/2009 | Kleinschmidt |
| 2002/0141912 | A1 | * | 10/2002 | Murrell et al. ............... 422/177 |
| 2004/0035418 | A1 | * | 2/2004 | Wiid ....................... 128/202.26 |
| 2004/0079367 | A1 | | 4/2004 | Goldblatt et al. |
| 2008/0115670 | A1 | * | 5/2008 | Hauville ............ B01D 46/0002 96/131 |

OTHER PUBLICATIONS

Chinese Second Office Action for Application No. 201210052766.5, dated Nov. 18, 2015, 5 pages excluding translation.
European Office Action for Application No. 11155922.5, dated Sep. 4, 2015, 5 pages.
Chinese Third Office Action for Application No. 201210052766.5, dated May 20, 2016, 3 pages excluding machine translation.

* cited by examiner

HOUSING FOR SOLID, FLUIDAL SUBSTANCE FOR REMOVING AN UNDESIRED RESPIRATORY GAS COMPONENT OF A RESPIRATORY GAS FLOW AND AN ARRANGEMENT FOR VENTILATING LUNGS OF A SUBJECT

BACKGROUND OF THE INVENTION

Field of the Invention

This disclosure relates generally to a housing for solid, fluidal substance for removing an undesired respiratory gas component of a respiratory gas flow and an arrangement for ventilating lungs of a subject.

Description of the Prior Art

Anesthesia machines are optimized for delivering anesthesia to a patient using volatile anesthetic agent liquids. In such systems, the anesthetic agent is vaporized and mixed into the breathing gas stream in a controlled manner to provide a gas mixture for anesthetizing the patient for a surgical operation. The most common volatile anesthetic agents are halogenated hydrocarbon chains, such as halothane, enflurane, isoflurane, sevoflurane and desflurane. Additionally, nitrous oxide ($N_2O$) can be counted in this group of volatile anesthetic agents, although the high vapor pressure of nitrous oxide causes nitrous oxide to vaporize spontaneously in the high pressure gas cylinder, where it can be directly mixed with oxygen. The anesthetizing potency of nitrous oxide alone is seldom enough to anesthetize a patient and therefore another volatile agent is used to support that.

Since the volatile anesthetic agents are expensive and are effective greenhouse gases that are harmful to the atmospheric ozone layer, anesthesia machines have been developed to minimize the consumption of the gases. To keep a patient anesthetized, a defined brain partial pressure for the anesthetic agent is required. This partial pressure is maintained by keeping the anesthetic agent partial pressure in the lungs adequate. During a steady state, the lung and body partial pressures are equal, and no net exchange of the anesthetic agent occurs between the blood and the lungs. However, to provide oxygen and eliminate carbon dioxide, continuous lung ventilation is required.

Anesthesia machines are designed to provide oxygen to the patient and eliminate carbon dioxide ($CO_2$), while preserving the anesthetic gases. To meet these goals a re-breathing circuit is used, in which a patient's exhaled gas is reintroduced for inhalation. Before re-inhalation, carbon dioxide must be removed from the gas, which is done with a carbon dioxide absorber. Before inhalation, the gas is supplied with additional oxygen and anesthetic agents based upon the patient demand. In this arrangement, the additional gas flow added to the re-breathing circuit can be less than 0.5 L/min although the patient ventilation may be 5-10 L/min. Such ventilation of the lung is carried out using a ventilator pushing inhalation gas with overpressure to the patient's lungs and then allowing that to flow out passively from the pressurized lungs to the breathing circuit.

Ventilation carries the breathing circuit oxygen to lungs for uptake to be burned in body metabolism. The outcome is $CO_2$ that diffuses to lungs and is carried out with exhalation gas. Before re-inhalation the gas is guided through an absorber for $CO_2$ removal. Effective $CO_2$ removal requires close contact with the breathing gas and the removing substance. To provide large contact area, the removing substance is therefore a surface of a porous structure of granules that fill a cartridge. The form of this granular structure is guided by flow resistance, the limitation of which is one of the key design goals of the breathing circuit. In an absorber optimized for minimal resistance, the gas flow path through the stacked granules is short and the flow distributes to a wide area. In such structure the gas flows slowly because the large surface area provides time for reaction between the gas and absorbent granules.

However, such optimal wide and short cartridge design involves a problem. Because the removing material is in granules, the granules may move in relation to each other. Packaging of the granules into a cartridge occurs in a factory, and thereafter the cartridge is transported to a customer site. The granules experience shaking during transportation which compresses the granules, increases the granule packaging grade and reduces the volume of the granule bed in the cartridge. Therefore the cartridge may have some empty space on its top when used. Because of the empty space, the gas flows through the absorber vertically, since when flowing horizontally the gas, which favors the route of the least resistance, would flow through the empty space without communication with the absorbent and thus allows the $CO_2$ to flow through the absorber.

When the gas flows vertically, the horizontal empty space is not harmful since the horizontal empty space does not disturb the internal flow resistance distribution within the cartridge. However, if the top surface of the granules is slanted as shown in FIG. 1, flow density at the low granule level, where the empty space 1 exists, increases over the areas of high level of granules 2. This is known as a flow channeling. A typical cartridge 3 comprises a gas input 4, a gas output 5 and mesh plates 6 and 7 for preventing granules therebetween to escape from the cartridge. A demand of $CO_2$ removal is proportional to the flow rate and the absorbent is consumed faster at the volumes of high gas flow. The absorbent volume in these areas is also smaller. Each of these factors causes fast absorbent wear-out at these high flow volumes. When all absorbent has been consumed, the $CO_2$ penetrates through the cartridge using the flow path where the capacity has been reduced, which increases the inspired patient gas $CO_2$ concentration. This signals the wear-out of the whole cartridge, even though unused material may still exist at the reduced flow volumes. Therefore, slanting reduces usable cartridge $CO_2$ removal capacity. The surface level of the granules may become slanted if inclined during unpacking and installing a cartridge having empty space caused during transportation.

BRIEF SUMMARY OF THE INVENTION

According to an embodiment of the present invention, there is provided a housing for a solid, fluidal substance for removing an undesired respiratory gas component of a respiratory gas flow. The housing comprises a space for receiving the solid, fluidal substance, a wall surrounding part of the space, a first separator surrounding part of the space, the first separator being configured to allow the respiratory gas to flow and to prevent the solid, fluidal substance from escaping from the space through the first separator, a second separator surrounding part of the space, the second separator being configured to allow the respiratory gas to flow and to prevent the solid, fluidal substance from escaping from the space through the second separator, and a limiter disposed between the first separator and the second separator, the limiter being configured to limit movement of the solid, fluidal substance inside the space, wherein one of the first separator and the second separator is configured to allow the respiratory gas to flow to the space and the remaining one of the first separator and the second separator is configured to allow the respiratory gas to flow from the space.

According to another embodiment of the present invention, there is provided a system for ventilating lungs of a subject. The system comprises a ventilator configured to supply a breathing gas for an inspiration and for receiving a breathing gas for an expiration, a gas mixer configured to supply a fresh gas for the subject's breathing, and a breathing circuit configured to connect the lungs of the subject, the ventilator and the gas mixer, wherein the breathing circuit comprises an inspiration limb configured to provide an inspiration gas including the fresh gas for the subject's breathing, an expiration limb configured to discharge an expiration gas, and a housing for a solid, fluidal substance for removing an undesired respiratory gas component of a respiratory gas flow, wherein the housing comprises a space for receiving the solid, fluidal substance, a wall surrounding part of the space, a first separator surrounding part of the space, the first separator being configured to allow the respiratory gas to flow and to prevent the solid, fluidal substance from escaping from the space through the first separator, a second separator surrounding part of the space, the second separator being configured to allow the respiratory gas to flow and to prevent the solid, fluidal substance from escaping from the space through the second separator, and a limiter disposed between the first separator and the second separator, the limiter being configured to limit movement of the solid, fluidal substance inside the space, wherein one of the first separator and the second separator is configured to allow the respiratory gas to flow to the space and the remaining one of the first separator and the second separator is configured to allow the respiratory gas to flow from the space.

BRIEF DESCRIPTION OF THE DRAWINGS

Various other features, objects, and advantages of different embodiments of the present invention will be made apparent to those skilled in art from the accompanying drawings and detailed description thereof. In the drawings.

DETAILED DESCRIPTION OF THE INVENTION

The above-mentioned shortcomings, disadvantages and problems are addressed herein which will be understood by reading and understanding the following specification.

Specific embodiments are explained in the following detailed description making a reference to accompanying drawings. These detailed embodiments can naturally be modified and should not limit the scope of the present invention as set forth in the claims.

Figure 1:
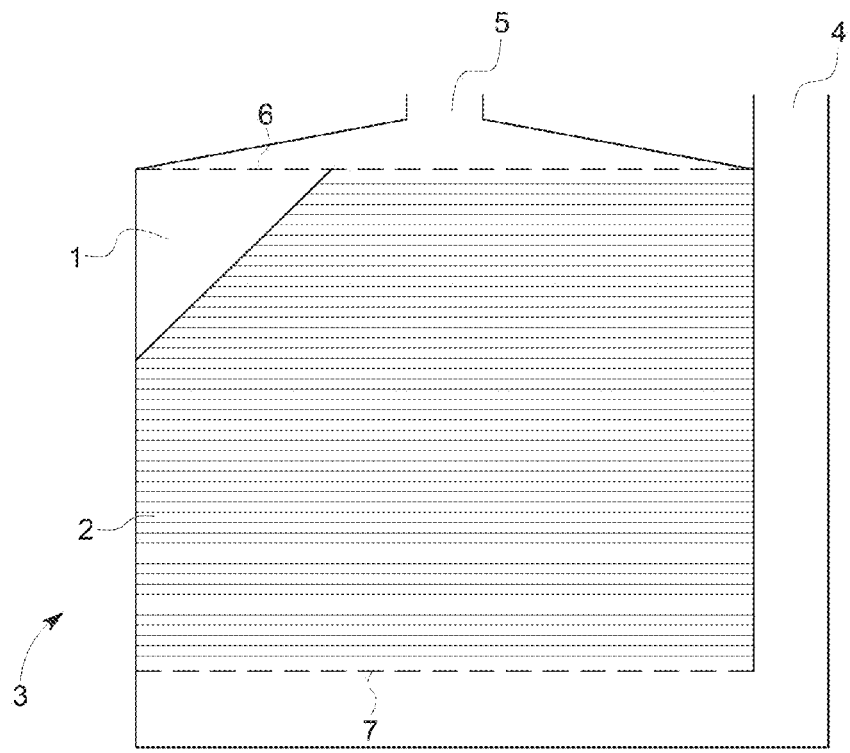
FIG. 1 is a schematic view of prior art cartridge when returned to normal position after tilting.
Figure 2:
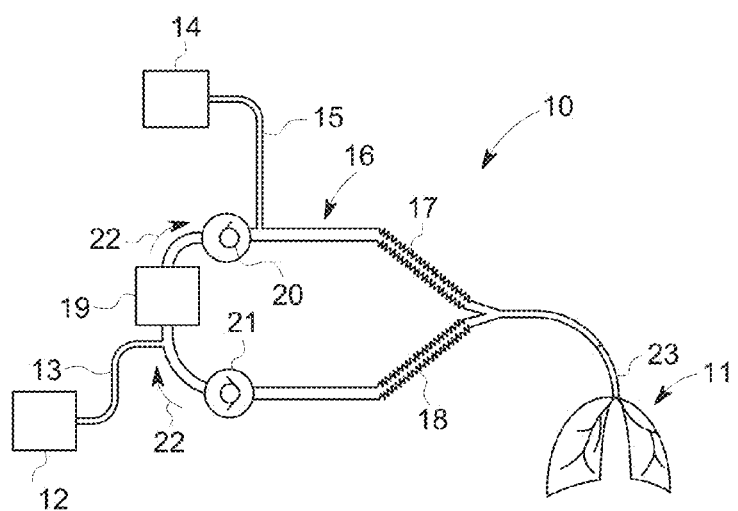
FIG. 2 illustrates an operational diagram of an arrangement for ventilating lungs of a subject in accordance with an embodiment of the present invention.

In FIG. 2, an arrangement 10 for ventilating lungs 11 of a subject is disclosed. The arrangement comprises a ventilator 12 which supplies breathing gas along a tube 13 to the lungs for an inspiration and receiving breathing gas for an expiration. The ventilator 12 may be of a well-known type e.g. drive gas based pneumatic flow-valve or mechanical piston driven. Also the arrangement comprises a gas mixer 14 which supplies fresh gas along a fresh gas tube 15 for the subject's breathing, a breathing circuit 16 connecting lungs 11 of the subject, the ventilator 12 and the gas mixer 14. The gas mixer 14 may comprise an anesthetic agent supply (not shown in the figure) such as an anesthetic agent vaporizer which provides anesthetic agent for the subject breathing.

The breathing circuit 16, which may be a re-breathing circuit, comprises an inspiration limb 17 providing an inspiration gas including the fresh gas for the subject's breathing and an expiration limb 18 which discharges an expiration gas. The ventilator controls the breathing circuit pressure through tube 13. Also the breathing circuit 16 comprises a housing 19 for a solid, fluidal substance such as granules for removing an undesired respiratory gas component of a respiratory gas flow. Typical solid, fluidal substance used in anesthesia is a carbon dioxide absorbing material, which may be soda-lime, a mixture of calcium hydroxide, sodium hydroxide, potassium hydroxide and water or any other substance that can extract $CO_2$ from a gas mixture e.g. molecular sieve or amines. The material may chemically react with carbon dioxide or otherwise remove it from the breathing gas. The housing 19 may be detachable from the breathing circuit 16. Typically the breathing circuit 16 also comprises directional valves 20 and 21 which guide the gas flow in the circuit in a direction indicated by arrows 22. For inhalation, the ventilator 12 increases the breathing circuit pressure by adding gas flow from tube 13. Directional valves 20 and 21 guide the gas flow through the housing 19 which includes the substance for removing an undesired respiratory gas component from the breathing gas. In this embodiment, the undesired respiratory gas component is carbon dioxide. The directional valves 20 and 21 guide the gas flow to the inspiration limb 17 and further along a subject's limb 23 to the subject's lungs 11. For expiration, the ventilator 12 releases gases from the breathing circuit through tube 13. For this purpose the ventilator 12 may, for example, operate an expiration valve (not shown in Figure). This will allow the gas flow from distended subject's lungs 11 through the subject limb 23 to the expiration limb 18 and further through the directional valve 21 to tube 13. The directional valve 20 prevents the gas flow from the subject's lungs 11 to enter the inspiration limb 17, thereby keeping the inspiration limb free from $CO_2$. Instead, the exhaled gas is rich with $CO_2$ that needs to be removed before being re-circulated for the inspiration, which is done in the housing 19 which includes the substance for removing an undesired respiratory gas component.

Figure 3:
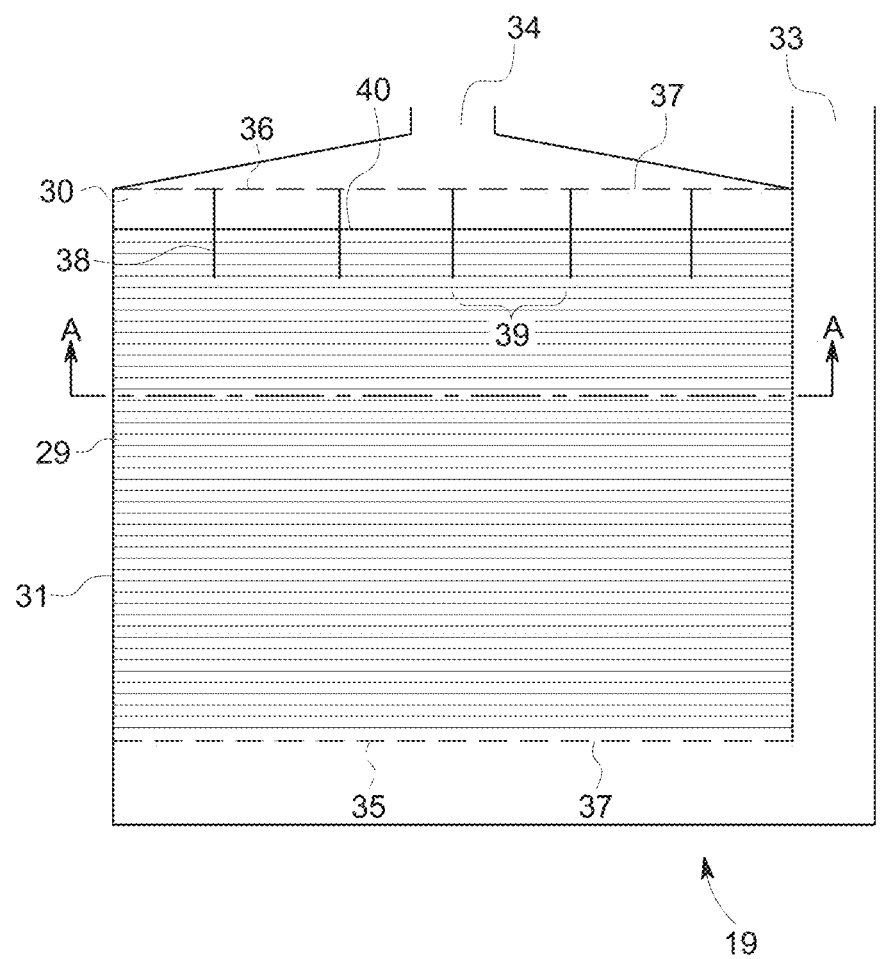
FIG. 3 is a schematic view of a housing for a solid fluidal substance for removing an undesired respiratory gas component of a respiratory gas flow in accordance with an embodiment of the present invention.

FIG. 3 presents a schematic drawing of the housing 19 comprising a space 30 receiving the solid fluidal substance 29 used in this embodiment to absorb carbon dioxide of the respiratory gas and a wall 31 surrounding a part of the space 30. Through a gas inlet 33 the respiratory gas flows to the housing 19 and is guided through the space filled with the solid fluidal substance 29 to the gas outlet 34 where it leaves the housing 19. Depending on the application, the gas may flow in either direction through the space 30 of the housing 19. The housing further comprises a first separator 35 and a second separator 36, which may be operatively connected or connectable to the wall. The first separator 35, which may be, for example, a mesh plate, allows the gas to flow but prevents the substance from escaping from the space 30 through the first separator 35 and the gas inlet 33. The second separator 36, which may be, for example, a mesh plate, allows the gas to flow but prevents the substance from escaping from the space 30 through the second separator 36 and the gas outlet 34. Since the gas may flow in either direction through the space 30 of the housing 19, one of the first separator 35 and the second separator 36 allows the respiratory gas to flow to the space and the remaining one of the first separator 35 and the second separator 36 allows the respiratory gas to flow from the space 30. The solid fluidal substance 29 is thus held within the housing 19 by the first separator 35 and the second separator 36. Gas is allowed to flow through openings 37 which hold the access of the absorbent granule of the solid fluidal substance 29 through these openings 37. The first separator 35 and the second separator 36 may be separate layers within the housing 19 as indicated on FIG. 3 or they may form the top and bottom ends of the housing depending on the breathing system connection interface. The gas inlet 33 and the gas outlet 34 may be separate from, and if desired, distant from the first separator 35 and the second separator 36. The first separator 35 can also be one of the gas inlet 33 and the gas outlet 34 and the second separator 36 can correspondingly be one of the remaining one of the gas inlet 33 and the gas outlet 34.

Figure 4:
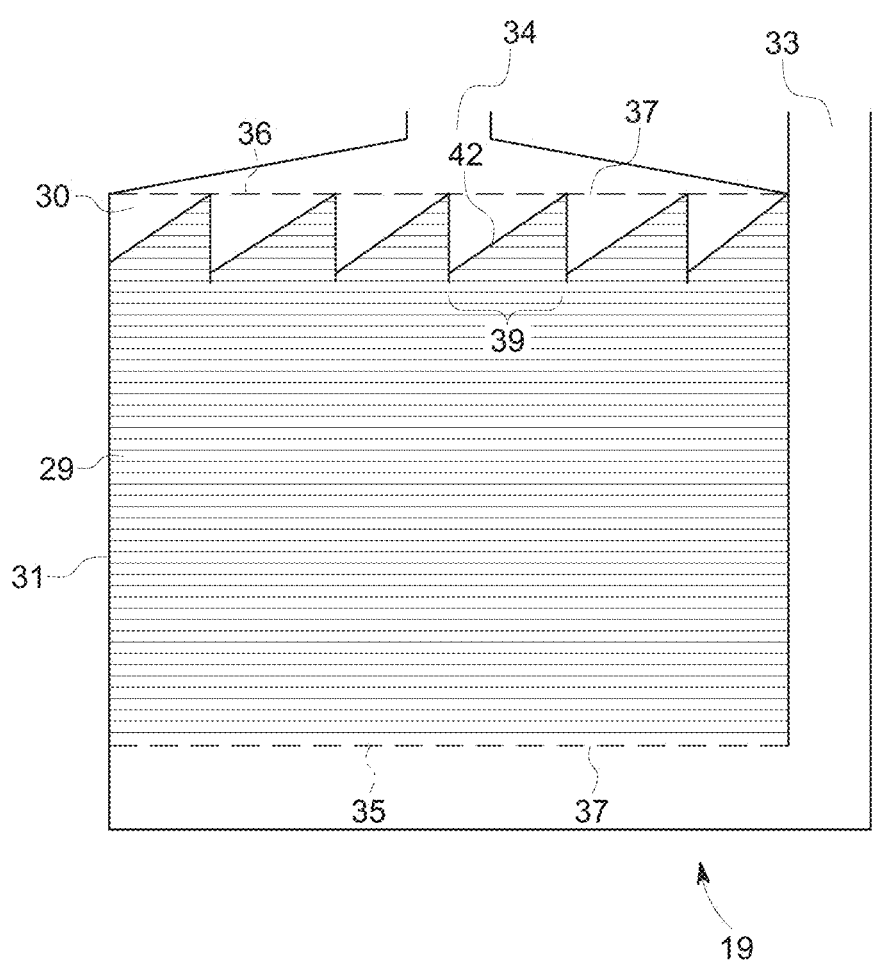
FIG. 4 shows a behavior of the substance when the housing of FIG. 3 has been returned to the normal position after tilting in accordance with an embodiment of the present invention.

The housing 19 further comprises a limiter 38 between the first separator 35 and the second separator 36 to limit movement of the solid fluidal substance 29 inside the space 30. In FIG. 3, from the top, the second separator 36 extends the limiter 38 towards the space 30 into the solid fluidal substance 29. Also, the limiter 38 can be extended from the first separator 35 towards the space 30 and into the solid fluidal substance 29. This is especially in a case where it is possible to turn the housing 19 upside down. The limiter 38 is positioned closer to one of the first separator 35 and second separator 36 than to midway between the first separator 35 and the second separator 36. Also both the limiter 38 and one of the first separator 35 and the second separator 36 can constitute an integral structure. The limiter 38 can also extend from both the first separator 35 and the second separator 36 towards the space 30 to ensure that the housing 19 can be assembled in both ways. Thus the limiter 38 can be an extension of one of the first separator 35 and the second separator 36 and can be long enough to reach the solid fluidal substance 29 even after packing of the granules of the solid fluidal substance 29 during transportation. The limiter 38 may extend from one of the first separator 35 and the second separator 36 towards the space 30 at least about 2.0 times, or more specifically about 2.5 times, a distance which is estimated to form between one of the first separator 35 and the second separator 36 and an upper level 40 of the solid fluidal substance 29 when compressed at the time taken into use. Even at the lowest level, the solid fluidal substance 29 extends vertically half-way up the dimension of the limiter 38. With this configuration, the solid fluidal substance 29, which is sloped because of tilting of the housing 19, remains distributed within individual compartments 39 conformed by the limiter as indicated in FIG. 4. Thus the compartments 39 formed by the limiter 38 can limit the movement of the solid fluidal substance 29 to various directions following one of the first separator 35 and the second separator 36 through the space 30. The limiter 38 can be also separated from one of the first separator 35 and the second separator 36, but still the limiter 38 may located close enough to limit the granules of the solid fluidal substance 29 from flowing through the respective separator 35, 36 when tilting.

The vertical dimension of the limiter 38 may be limited since all walls may enhance the channeling effect. Therefore, uniform volume of the granules of the solid fluidal substance 29, either before or after the penetrating respiratory gas enters the limiter 38 area, is beneficial to guarantee effective $CO_2$ removal despite potential local channeling caused by the limiter 38.

The maximum angle the granules of the substance can settle determines the optimal dimension of the limiter 38, including a horizontal distance of the adjacent extensions and a vertical height or depth of the limiter 38. Depending on the granules of the solid fluidal substance 29, maximum sloping angle 42 can be up to 45 degrees, as shown in FIG. 4. Therefore the vertical height and horizontal distance of the limiter is advantageously equal. If the potential sloping angle is smaller, the horizontal distance may be longer than the vertical height. A horizontal distance smaller than a vertical height does not provide any additional benefit but may instead prevent filling of the limiter 38 area. For practical solutions of different granules, the ratio of the horizontal distance to vertical height may vary from 2:1 to 1:1. Typically, the packaging of the solid fluidal substance 29 leaves less than 10% vertical empty space below the top separator, which may be one of the first separator 35 and the second separator 36 depending on which one is upwards. If the height of the volume of the substance is about 10 cm, the empty space may thus be about 1.0 cm and the required vertical dimension of the limiter 38 is then at least about 2.0 cm or even about 2.5 cm, which may also be the horizontal distance of the limiter compartment 39.

Figure 5:
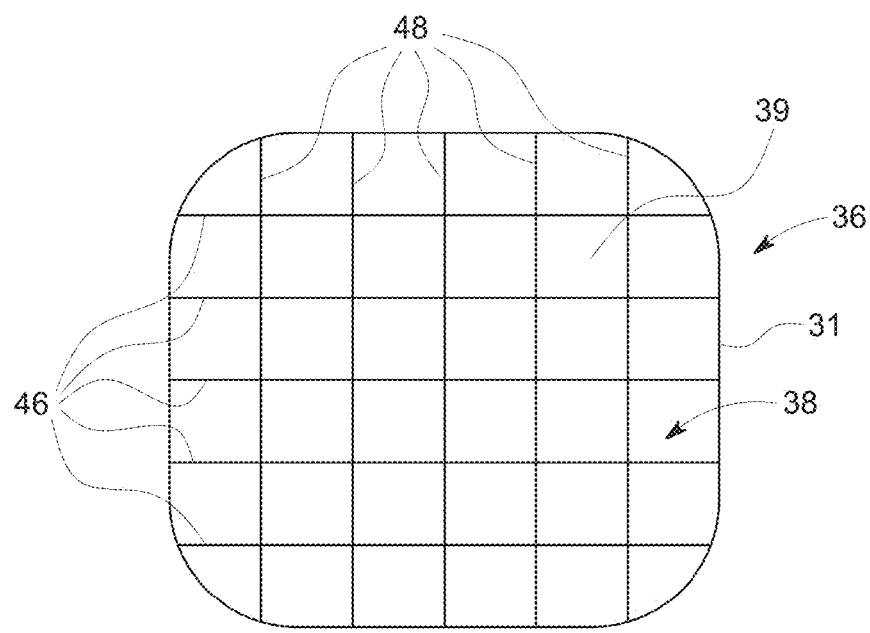
FIG. 5 is a cross section of the housing of FIG. 3 taken along lines A-A in accordance with an embodiment of the present invention.

FIG. 5, which is a cross-section of the housing 19 of FIG. 3 along lines A-A, shows an embodiment of the present invention wherein the second separator 36 and the limiter 38 constitute an integral structure. The limiter 38 comprises a first set of adjacent extensions 46 forming a continuous structure following the second separator 36 through the space 30 when the housing 19 is in the upright position and the second separator 36 is substantially in the horizontal position, in which case the respiratory gas flows through the space 30 in a substantially vertical direction. The limiter shown in FIG. 5 also comprises a second set of adjacent extensions 48 which may also form a continuous structure following the second separator 36 through the space 30 when the housing 19 is in an upright position and the second separator 36 is substantially in the horizontal position, in which case the respiratory gas flows through the space in a substantially vertical direction. The first set of adjacent extensions 46 and the second set of adjacent extensions 48 are crossing and form intersecting walls that form compartments 39. The first set of adjacent extensions 46 may form an angle of between about 60-90 degrees, more specifically about 70-90 degrees, or even more specifically about 80-90 degrees, with the second set of adjacent extensions 48. Adjacent extensions of the first set 46 can be substantially parallel with each other. Also adjacent extensions of the second set 48 can be substantially parallel with each other.

It should be understood that FIG. 5 could also describe the first separator 35 with the limiter 38 having the same construction.

Figure 6:
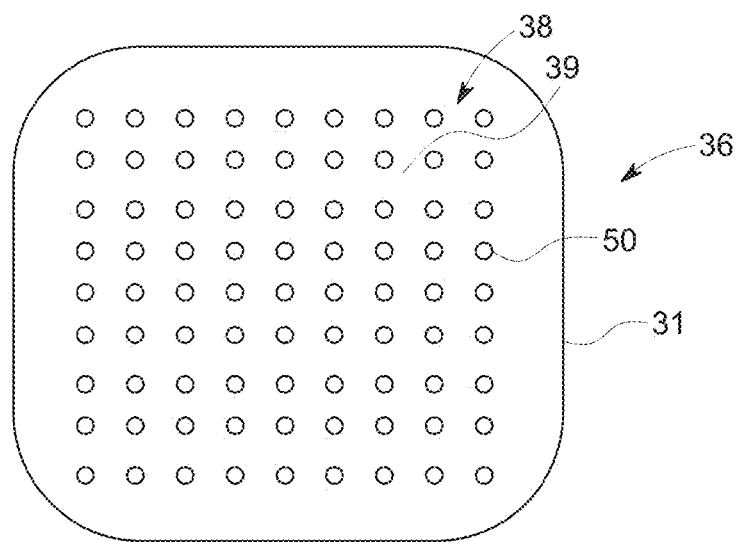
FIG. 6 is a cross section of the housing of FIG. 3 along lines A-A according to an embodiment of the present invention.

FIG. 6 shows a cross-section of the housing 19 of FIG. 3 along lines A-A according to an embodiment of the present invention, wherein the second separator 36 and the limiter 38 constitute and integral structure. The limiter 38 comprises a set of pins 50, constructed to form compartments 39 between the set of pins 50. The compartments 39 follow the second separator 36 through the space 30 when the housing 19 is in the upright position and the second separator 36 is substantially in the horizontal position, and in which case the respiratory gas flows through the space 30 in a substantially vertical direction. The dimensional calculation above applies only for the structure of FIG. 5. The pins 50 must be denser than adjacent extensions having continuous structure as shown in FIG. 5, because the granules of the substance may flow between the pins. Thus the distance between different pins can be from about 5.0 to about 15 mm, more specifically from about 7.0 to about 13 mm, or even more specifically about 10 mm. Also other types of compartments 39, for example a honeycomb, would meet the requirement of FIGS. 5 and 6. The structures disclosed in FIGS. 5 and 6 limit the movement of the solid fluidal substance 29 independently of tilting direction and thus the compartmental division may occur in both horizontal directions. It should be understood that FIG. 6 can be applied to the first separator 35 with the limiter 38 having the same construction.

Figure 7:
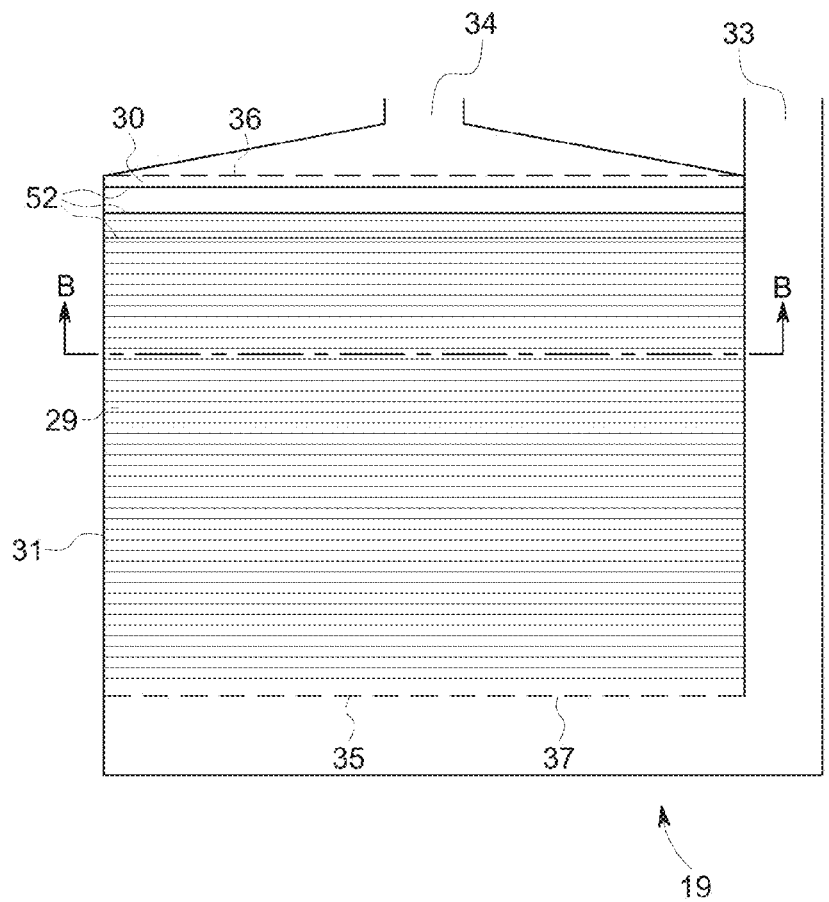
FIG. 7 is a schematic view of a housing for a solid, fluidal substance for removing an undesired respiratory gas component of a respiratory gas flow in accordance with an embodiment of the present invention.
Figure 8:
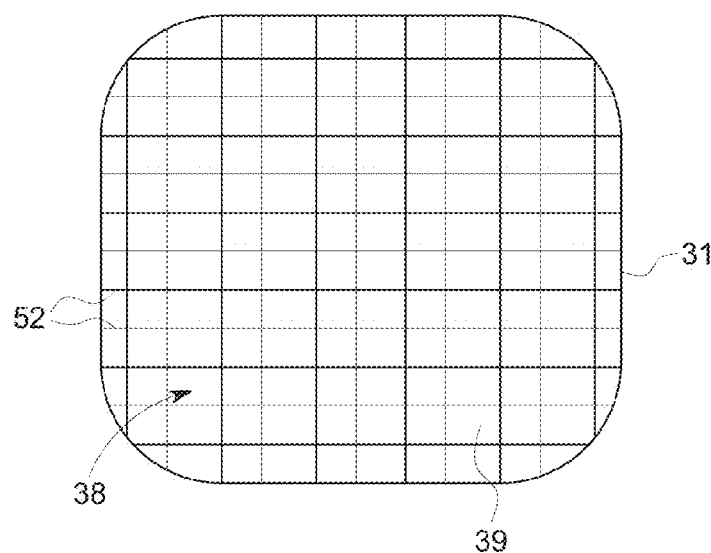
FIG. 8 is a cross section of the housing of FIG. 7 taken along lines B-B according to an embodiment of the present invention.

FIGS. 7 and 8 show an embodiment of the present invention which is similar to the embodiment of FIG. 3. The limiter 38 comprises a set of nets 52 one on the other. The nets 52 are in a horizontal position being substantially parallel with the second separator 36. Compartments 39 are formed between the nets. Distance between the nets 52 and the closest net to the second separator 36 can be smaller than about 10 mm. Distance between parallel net threads can be smaller than about 20 mm. The nets 52 may be interleaved to provide better grid against movement of the fluidic granules when tilting. It should be understood that FIGS. 7 and 8 can be applied to the first separator 35 having the limiter 38 having the same properties.

As explained above, the embodiments disclose a housing 19 and arrangements where slanting of a solid fluidal substance 29, especially a $CO_2$ removing substance, is limited in an incompletely filled housing 19. For this purpose, the top of the housing 19 has the limiter 38 extending into the solid fluidal substance 29, which may comprise absorbent granules. The limiter 38 may extend to the top surface of the solid fluidal substance 29 accommodating any empty space within the housing 19 because of incomplete filling or stacking of the solid fluidal substance 29 during transportation. When tilting of the housing 19 occurs, limits flow of granules of the solid fluidal substance 29 to one side of the housing 19 and leaves empty space to the other side of the housing 19 when the housing 19 is returned to a normal position. The limiter 38 disclosed in embodiments of the present invention distributes this one empty space to a number of small compartments 39 within the volume formed by the limiter 38. As a result, the height differences of the lows and highs of the surface of the solid fluidal substance 29 is reduced when the empty space of the housing remains more evenly distributed at the top of the housing 19, as shown in FIG. 4. The reduction of the height differences maintains even flow distribution throughout the space filled with the solid fluidal substance 29, reduces the channeling, and thus improves the usage of the solid fluidal substance 29, especially for $CO_2$ removal capacity.

The written description uses examples to disclose the embodiments of the present invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A system for ventilating lungs of a subject, the system comprising:
   a ventilator configured to supply a breathing gas for an inspiration and for receiving a breathing gas for an expiration;
   a gas mixer configured to supply a fresh gas for a subject's breathing; and
   a breathing circuit configured to connect the lungs of the subject, the ventilator and the gas mixer, wherein the breathing circuit comprises an inspiration limb configured to provide an inspiration gas including the fresh gas for the subject's breathing, an expiration limb configured to discharge an expiration gas, and a housing for a solid, fluidal substance for removing an undesired respiratory gas component of a respiratory gas flow, wherein the housing comprises:
      a space for receiving the solid, fluidal substance;
      a wall surrounding part of the space;
      a bottom separator surrounding part of the space, the bottom separator being configured to allow the respiratory gas to flow and to prevent the solid, fluidal substance from escaping from the space through the bottom separator;
      a top separator surrounding part of the space, the top separator being configured to allow the respiratory gas to flow and to prevent the solid, fluidal substance from escaping from the space through the top separator; and
      a limiter disposed between the bottom separator and the top separator, the limiter comprising a plurality of nets, the limiter being configured to limit movement of the solid, fluidal substance inside the space, wherein in a cross-sectional view interleaved threads of one of the plurality of nets are offset from interleaved threads of another of the plurality of nets to allow the solid, fluidal substance to settle within the space such that a portion of the top surface of the solid, fluidal substance has a sloping angle,
      wherein one of the bottom separator and the top separator is configured to allow the respiratory gas to flow to the space and the remaining one of the bottom separator and the top separator is configured to allow the respiratory gas to flow from the space, wherein the substance is configured to leave empty space below the top separator, and wherein the limiter is disposed adjacent the top separator.

2. The system according to claim 1, wherein the limiter is disposed closer to the top separator than to midway between the bottom separator and the top separator.

3. The system according to claim 1, wherein a distance between parallel net threads are greater than a distance between nets.

4. The system according to claim 1, wherein the solid, fluidal substance is a chemical compound for removing carbon dioxide.

5. The system according to claim 1, wherein the limiter is configured to form compartments to limit the movement of the solid, fluidal substance in various directions through the space.

6. A housing for a solid, fluidal substance for removing an undesired respiratory gas component of a respiratory gas flow, the housing comprising:
   a space for receiving the solid, fluidal substance;
   a wall surrounding part of the space;
   a bottom separator surrounding part of the space, the bottom separator being configured to allow the respiratory gas to flow and to prevent the solid, fluidal substance from escaping from the space through the bottom separator;
   a top separator surrounding part of the space, the top separator being configured to allow the respiratory gas to flow and to prevent the solid, fluidal substance from escaping from the space through the top separator; and
   a limiter disposed between the bottom separator and the top separator, the limiter comprising a plurality of non-hollow pins integrated with the top separator, the limiter being configured to limit movement of the solid, fluidal substance inside the space, the plurality of non-hollow pins having a density configured to allow the solid, fluidal substance to settle within the space such that a portion of the top surface of the solid, fluidal substance has a sloping angle,
   wherein one of the bottom separator and the top separator is configured to allow the respiratory gas to flow to the space and the remaining one of the bottom separator and the top separator is configured to allow the respiratory gas to flow from the space, wherein the substance is configured to leave empty space below the top separator, and wherein the limiter extends from the top separator partially toward the bottom separator.

7. The housing according to claim 6, wherein the solid, fluidal substance is a chemical compound for removing carbon dioxide.

8. The housing according to claim 6, wherein the limiter is configured to form compartments to limit the movement of the solid, fluidal substance in various directions through the space.

* * * * *